US009416222B2

(12) United States Patent
Schulze et al.

(10) Patent No.: US 9,416,222 B2
(45) Date of Patent: Aug. 16, 2016

(54) QUALITY TEST FOR POLYMERIZABLE LACTIC ACID AND METHOD FOR PRODUCING SAME

(71) Applicants: Joachim Schulze, Soest (DE); Rainer Hagen, Berlin (DE); Wolfgang Tietz, Biendorf (DE); Shashank Ghanegaonkar, Leipzig (DE)

(72) Inventors: Joachim Schulze, Soest (DE); Rainer Hagen, Berlin (DE); Wolfgang Tietz, Biendorf (DE); Shashank Ghanegaonkar, Leipzig (DE); Udo Mühlbauer, Berlin (DE); Willi Techlin, Berlin (DE)

(73) Assignees: THYSSENKRUPP INDUSTRIAL SOLUTIONS AG, Essen (DE); UHDE INVENTA-FISCHER GMBH, Berlin (DE)

( * ) Notice: Subject to any disclaimer, the term of this patent is extended or adjusted under 35 U.S.C. 154(b) by 88 days.

(21) Appl. No.: 14/356,038

(22) PCT Filed: Oct. 22, 2012

(86) PCT No.: PCT/EP2012/004407
§ 371 (c)(1),
(2) Date: May 2, 2014

(87) PCT Pub. No.: WO2013/064219
PCT Pub. Date: May 10, 2013

(65) Prior Publication Data
US 2014/0323682 A1    Oct. 30, 2014

(30) Foreign Application Priority Data

Nov. 4, 2011  (DE) .......................... 10 2011 117 625
Feb. 10, 2012  (DE) .......................... 10 2012 002 498

(51) Int. Cl.
*C08G 63/08*    (2006.01)
*C12P 7/56*    (2006.01)
(Continued)

(52) U.S. Cl.
CPC ................ *C08G 63/08* (2013.01); *C08G 63/89* (2013.01); *C08G 63/90* (2013.01); *C12N 1/02* (2013.01);
(Continued)

(58) Field of Classification Search
None
See application file for complete search history.

(56) References Cited

U.S. PATENT DOCUMENTS 5,023,349 A    6/1991  Bhatia
5,043,458 A    8/1991  Bhatia
(Continued)

FOREIGN PATENT DOCUMENTS

DE    19902897        8/2000
DE    19902897 A1    8/2000
(Continued)

OTHER PUBLICATIONS

Machine Translation of WO 2010003534, Google Patents.*
(Continued)

*Primary Examiner* — Karl J Puttlitz
(74) *Attorney, Agent, or Firm* — thyssenkrupp North America, Inc.

(57) ABSTRACT

Disclosed is a test and test apparatus used to determine whether lactic acid is suitable for polymerization. The test apparatus comprises a) means for the polycondensation of the lactic acid to form a pre-polymer, b) means for depolymerization of the prepolymer to form dilactide, and c) means for carrying out analytical methods to determine at least one of the dilactide yield and/or the racemization, wherein lactic acid which is suitable for polymerization exhibits a dilactide yield of >90% and a racemization of <5%.

16 Claims, 2 Drawing Sheets

(51) Int. Cl.
    *G01N 33/04*     (2006.01)
    *C08G 63/90*     (2006.01)
    *C08G 63/89*     (2006.01)
    *C12N 1/02*     (2006.01)
    *G01N 33/44*     (2006.01)

(52) U.S. Cl.
    CPC . *C12P 7/56* (2013.01); *G01N 33/04* (2013.01); *G01N 33/442* (2013.01); *Y10T 436/201666* (2015.01)

(56) References Cited

U.S. PATENT DOCUMENTS

| | | | |
|---|---|---|---|
| 5,136,057 A | | 8/1992 | Bhatia |
| 5,177,008 A | * | 1/1993 | Kampen ............ C12F 3/10 435/139 |
| 2002/0132967 A1 | | 9/2002 | Ohara |
| 2006/0014975 A1 | | 1/2006 | Coszach |
| 2011/0263811 A1 | | 10/2011 | Sawai |

FOREIGN PATENT DOCUMENTS

| | | |
|---|---|---|
| DE | 69815369 T2 | 5/2004 |
| DE | 102007045701 B3 | 5/2009 |
| DE | 102009019248 A1 | 11/2010 |
| EP | 0986532 B2 | 10/2006 |
| EP | 2030679 | 3/2009 |
| EP | 2030679 A1 | 3/2009 |
| WO | 9606092 | 2/1996 |
| WO | 2006/124633 A1 | 11/2006 |
| WO | 2009/030397 A1 | 3/2009 |
| WO | 2010003534 * | 1/2010 |

OTHER PUBLICATIONS

English language Abstract of Saara Inkinen et al.: "From Lactic Acid to Poly(lactic acid) (PLA): Characterization and Analysis of PLA and Its Precursors," Biomacromolecules, Mar. 14, 2011, pp. 523-532, vol. 12, No. 3.
English Language translation of International Search Report for International Patent application No. PCT/EP2012/004407.
Original German Language International Search Report for International Patent application No. PCT/EP2012/004407.
Saara Inkinen et al.: "From Lactic Acid to Poly(lactic acid) (PLA): Characterization and Analysis of PLA and Its Precursors," Biomacromolecules, Mar. 14, 2011, pp. 523-532, vol. 12, No. 3.
J. Dahlmann et al, British Polymer Journal, Bd. 23 (1990), p. 235. 240.
English language abstract of DE19902897 (C2).
English language abstract of EP2030679.
English language abstract of EP0986532.
English language abstract of DE102007045701.
English language abstract of DE69815369.
English language abstract of DE102009019248.
English language abstract of WO2009/030397.

* cited by examiner

QUALITY TEST FOR POLYMERIZABLE LACTIC ACID AND METHOD FOR PRODUCING SAME

CROSS REFERENCE TO RELATED APPLICATIONS

This application is a U.S. National Stage Entry of, and claims priority to, International Patent Application Serial Number PCT/EP2012/004407, filed Oct. 22, 2012, which claims priority to German Patent Application Serial Nos. DE102011117625.3, filed Nov. 4, 2011, and DE102012002498.3, filed Feb. 10, 2012.

FIELD

This disclosure relates to quality tests for polymerizable lactic acid and methods of producing the same.

BACKGROUND

The production of lactic acid from carbohydrate-containing materials by fermentation is increasingly gaining in importance. However, other possibilities for the obtention of lactic acid via chemical transformations of reactants which derive from petrochemistry, such as for example the hydrolysis of lactonitrile, are also known to those skilled in the art. Lactic acid is an environmentally harmless intermediate for the production of cleaning agents, liquid soaps, scale removers and textile additives. Interest in lactic acid has further increased recently since the polymeric form of lactic acid, polylactide, is compostable. Polylactide or polylactic acid is used as a biologically degradable and well tolerated plastic in the food industry, in cosmetics and in medical technology. There is particular interest in carrier bags made of compostable polylactic acid films, since carrier bags made of conventional plastic are not degraded in the environment and are therefore a major environmental pollutant. In contrast, plastic carrier bags made of polylactic acid are biologically degradable and thus an environmentally harmless alternative to carrier bags made of conventional plastic.

Lactic acid occurs in two diastereoisomeric forms, as L(+)- and D(−)-lactic acid. The starting material for the fermentative production of lactic acid is a carbohydrate-containing material, which is transformed into lactic acid by treatment with microorganisms suitable for this. Suitable bacteria for this are for example lactic acid bacteria from the genus of the Lactobacillaceae, but also microorganisms from the genus of the *Saccharomyces* or *Rhizopus*. Depending on the genus of the microorganisms used, one or both of the aforesaid diastereoisomeric forms of lactic acid are obtained.

Decisive for the industrial utilization of lactic acid which is generated by fermentation of carbohydrate-containing substrates by various microorganisms is the economy and efficiency of the separation and purification of the lactic acid from these aqueous fermentation solutions, which apart from the lactic acid or the lactic acid salts also contain further organic acids, other side products of the fermentation, microorganisms and components thereof and residues of the substrates, such as sugar.

These impurities interfere in a subsequent polymerization of the lactic acid to polylactic acid and thus in the production of biologically degradable plastics. It has long been known, and for example follows from J. Dahlmann et al, British Polymer Journal, Bd. 23 (1990), p. 235. 240, that extremely pure monomer has to be used in order to achieve a high degree of polymerization of the lactic acid. In order to achieve the desired high degree of polymerization, the lactic acid after passing through purification must have a concentration of 80 wt. %.

From the literature, a large number of methods relating to the purification of lactic acid are known.

For example, the teaching in some patents is to use distillation for the purification of lactic acid from aqueous solutions. Such a process is used in EP 0986532 B2. In DE 10 2007 045 701 B3, a combined extraction with linear n-trioctylamine (TOA) and a distillation is disclosed. Further possibilities known in the literature are electrodialysis or esterification with an alcohol, after which likewise distillation and then hydrolysis of the ester formed are performed. These processes are extremely cost-intensive. Moreover, distillation has the disadvantage that a part of the carbohydrates is always also simultaneously extracted, which results in worsening of the yield of the whole process and complicates the isolation of the product.

Processes using calcium hydroxide and sulfuric acid, wherein gypsum is formed in large quantities as a side product, are also known. In this connection it was moreover found that lactic acid can for example be isolated from a fermentation broth acidified with sulfuric acid, which as well as free lactic acid also contains ammonium and sulfate ions, by chromatographic methods. DE 69815369 T2 for example inter alia describes the separation of lactic acid from aqueous mixtures by adsorption onto a solid adsorbent, and preferably a solid adsorbent which adsorbs lactic acid versus lactate is used here.

In particular, according to the above document, weak anion exchangers are possible for the isolation of lactic acid. Further, DE 10 2009 019 248 A1 describes chromatographic methods for the purification of organic acids, especially of lactic acid, by the use of simulated moving bed chromatography.

WO 2006/124633 A1 describes a process for the production of ammonium lactate by fermentation. In the fermentation, the ammonium salt of lactic acid is formed, which can be separated from the fermentation solution e.g. by extraction. The ammonium salt can very easily be cleaved in a subsequent step with weak acids or carbon dioxide. The free lactic acid is thereby obtained, which can then be purified for example by distillation.

A disadvantage of many processes is that additional substances are added to the process, which must no longer be contained in the product or whereof traces in the target product can result in limitations in the quality and usability of the product. Thus the purification processes from the state of the art often result in inadequate quality of the purified lactic acid and polymerization to polylactic acid is not possible to the desired extent. The practical implementation of the processes is also sometimes associated with considerable technical and energy expenditure. The quality of the purified lactic acid often first becomes apparent when polylactic acid is to be produced.

SUMMARY

The purpose of the invention is to provide a test for determining the quality of lactic acid, which makes it possible before the production of polylactic acid to establish whether the lactic acid present is a polymerizable material. In addition, a process for separation and purification of lactic acids from fermentation liquors should be provided, which fulfils the quality criteria for a polymerizable material, which are determined with the test for quality determination and avoids known disadvantages of other processes.

According to the invention, the problem is solved by the use of a test for determining the quality of lactic acid, comprising a) means for polycondensation of the lactic acid to a prepolymer
b) means for depolymerization to the dilactide, and
c) means for carrying out analytical methods for determination of the dilactide yield and/or the racemization, wherein lactic acid which fulfils the test and is suitable for polymerization exhibits a dilactide yield of >90% and a racemization of <5%.

This test for quality determination allows to determine the suitability of a lactic acid sample for the production of polylactic acid. The stated dilactide yields and the racemization of <5% can for example be attained with the apparatuses described in examples 1 and 2 and the technical process conditions described there. The test according to the invention consists of two parts: the polycondensation of the lactic acid and the depolymerization of the polycondensate to lactide.

Advantageously, the lactic acid used in the test for quality checking exhibits a dilactide yield of >93%. Furthermore it is advantageous if the lactic acid used in the test for quality checking exhibits a racemization of <3%. These are the criteria preferably to be attained by the process for quality determination of lactic acid, so that the lactic acid is suitable for a polymerization.

In the polycondensation, lactic acid, which should preferably be 88% to 92%, is heated stepwise over a time-span of 5 to 7 hours from 120° C. to 180° C. and the pressure simultaneously decreased from 350 mbar to 450 mbar to 100 mbar to 25 mbar. Furthermore, in process step a) after a time-span of 1 to 3 hours at a temperature of 130° C. to 160° C. and a pressure of 150 mbar to 250 mbar, a catalyst is added, wherein the catalyst is preferably butyltin oxide. Thereby by increasing the temperature stepwise and simultaneous reduction of the pressure within six hours, the lactic acid to be tested is polycondensed to a prepolymer.

Further, the prepolymer obtained in the polycondensation is sent for analytical procedures for the determination of the molecular mass, wherein the carboxyl terminal groups are preferably determined. For this, the PLA oligomer is dissolved in acetone. After addition of methanol, the solution is titrated with 0.1 N benzyl alcoholic KOH solution. The endpoint is detected by potentiometry. From the carboxyl terminal group concentration ("COOH"), measured in mmol/kg, the number average of the molecular mass can be calculated according to the equation $$M_n = \frac{10^6}{COOH}.$$

The rise in the molecular weight over time already enables a first estimation of the quality of the lactic acid.

The required means for polycondensation comprise a three-necked round-bottomed flask with stirrer, temperature sensor and fitted fractionating column. The flask is immersed in an oil-bath which is heated with a hotplate. At the head of the fractionating column there is fitted a reflux condenser which is kept at 50° C. to 70° C. with temperature-controlled water. Above the reflux condenser there is placed a Liebig condenser cooled with cold water, which opens into a vessel. Side products of the polycondensation such as water collect there. Accompanying lactic acid is separated from the water in the column and flows back into the polycondensate. A vacuum pump is connected to the apparatus via a side connector at the outlet of the Liebig condenser. The vacuum is adjusted by means of a needle valve. Components not condensable at the condenser temperature are removed before the vacuum pump by means of a cold trap for example cooled with dry ice. In general, any design for the polycondensation of lactic acid deviating therefrom known to those skilled in the art is possible.

In the depolymerization, the prepolymer obtained in the polycondensation, which is present in the three-necked round-bottomed flask, is first held for 1.5 to 2.5 hours at a temperature of 150° C. to 215° C. and a pressure of 180 to 220 mbar and the pressure is then decreased stepwise to a range of 50 to 3 mbar. During this, the lactide formed from the prepolymer is weighed preferably hourly in order to reconcile the weight determined with the results of the analytical methods to be performed in process step c).

For the depolymerization to dilactide, the described means for polycondensation are modified such that the fractionating column is arranged next to the three-necked round-bottomed flask and connected with this via a bridging tube so that the vapor from the round-bottomed flask can flow from bottom to top through the fractionating column and no reflux from the fractionating column into the three-necked flask is possible. The dilactide formed escapes in vapor form from the flask, condenses in the reflux condenser of the column and collects in a separate round-bottomed flask which closes the column at the bottom. Side products such as water and lactic acid condense in the Liebig condenser at the head of the fractionating column and collect in the vessel.

The dilactide generated in the depolymerization is passed to the means for performing analytical methods for the determination of the racemization and/or the dilactide conversion, which is effected for example via separation via an HPLC and subsequent measurement by means of a UV detector. In this manner, the lactide yield (lactide created based on the prepolymer used) and the enantiomeric purity of the lactide are determined. For this, the lactide sample is dissolved in a mixture of 90/10 ml/ml n-hexane/ethanol. The dissolved components are separated by HPLC on a chiral column and analyzed with a UV detector at 223 nm. From this, the degree of racemization and the dilactide conversion are calculated according to the following equations:

(1) Calculation of the racemization:

$$Rac = \frac{\sum m_i \cdot (w_{i,meso} + w_{i,D})}{\sum m_i}$$

$m_i$: mass of the lactide sample i)
$w_{i,meso}$: mass fraction of mesolactide in the lactide sample i
$w_{i,D}$: mass fraction of D-lactide in the lactide sample i (2) Calculation of the conversion:

$$Conversion = \frac{\sum m_i}{m_{PP}}$$

$m_{PP}$: weight of the prepolymer after the polycondensation

Also a subject of the present invention is a process for separation and purification of polymerizable lactic acid from fermentation liquors, which exhibits a dilactide yield of >90% and a racemization of <5%. These values are determined by means of the quality test according to the invention and indicate a polylactic acid which is suitable for polymerization.

In a preferred configuration of the process for separation and purification of lactic acid from fermentation liquors are comprised the process steps
  a) a separation of the biomass and any solids present from the fermentation liquor in at least two successive steps,
  b) a separation of lactic acid solution from the biomass-free fermentation liquor by simulated moving bed chromatography (SMB),
  c) a purification by ion exchange,
  d) a first single or multistage evaporation step,
  e) a purification by ion exchange,
  f) a second single or multistage evaporation step.

With this process, a lactic acid is produced which exhibits high product purity of >80 wt. %.

In a preferred configuration of the process, the purification by ion exchange in process step c) is combined with a nanofiltration, wherein the purification by ion exchange and nanofiltration are arranged in any order. An effective fine purification thereby occurs.

The fermentation liquor, which contains the lactic acid in the form of ammonium lactate, biomass and components of the substrate, is continuously fed into a precoat filtration and/or a microfiltration and/or a centrifugation. In this, the temperature and pH correspond to the values for the fermentation, since it was established that through inactivation of the biomass by raising the temperature and lowering the pH by addition of acid autolysis of the biomass is accelerated and more lysis products are released into the fermentation liquor. Also the time between ending of the fermentation and the separation of the biomass should be kept as short as possible and should be not more than 2 hrs, and preferably be less than 1-2 hrs. The biomass concentration in the filtrate should not exceed 1 g/l. The end product quality is favorably influenced by this procedure.

The filtrate from the precoat or microfiltration is passed in process step a) to a second stage which consists of a single or two-stage ultrafiltration. Here residual biomass fractions, insoluble solids and higher molecular weight compounds are removed. Membranes with a separation limit of 0 kDa were identified as the optimum between product quality and flow rates of the membranes. Because of the solubility coefficients of ammonium lactate in water, the temperature of the liquid media should be 30° C. The retentate is recycled for precoat or microfiltration or alternatively collected and used as the starting product for the production of technical quality dicarboxylic acid and the permeate is fed into the further process steps.

In the ultrafiltration permeate the lactic acid is present in the form of its salt as ammonium lactate. For its conversion to the lactic acid, addition and admixture of concentrated sulfuric acid and associated with this a lowering of the pH of the solution to values between 2.2 to 2.4 are effected. Here, the acidification is performed in two steps, wherein in a 1st step the fermentation liquor from the first stage of the process step a) is acidified with concentrated sulfuric acid to a pH of 4.4 to 4.6, and in a $2^{nd}$ step the ultrafiltration permeate from the second stage of the process step a) is acidified with concentrated sulfuric acid to a pH of 2.0 to 2.4, so that the salt of lactic acid contained in the purified fermentation solution is converted to lactic acid and a salt is formed in the stoichiometric proportion. Here ammonium sulfate is formed in the stoichiometric proportion. To avoid undesired precipitation, this process step is effected at temperatures between 30° C. to 60° C. and preferably in a range between 30° C. to 40° C. This prepurified solution is available for the separation and purification of the lactic acid.

The separation of the acidic ultrafiltration permeate is effected in a simulated moving bed chromatography. This is a particularly efficient modification of high performance liquid chromatography, wherein a large number of theoretical plates is brought about through the succession of several separating columns mutually connected via valves in a continuous loop and the separation efficiency of the chromatography is considerably improved. Cation exchangers and anion exchangers are used as the stationary phase.

On the basis of the different retention times for lactic acid and ammonium sulfate, separation of the two main components takes place. Demineralized water and/or vapor condensate are used as the eluent. It could be shown that in the extract more than 95% of the lactic acid contained in the ultrafiltration permeate can be recovered, wherein the ratio between ultrafiltration permeate and eluent in the range varies between 1:1 and 1:2.5 and eight anion exchanger columns connected in a continuous loop were used. The extract still contains only small quantities of ammonium sulfate, acetic acid and colored materials from the fermenter liquor. The eluted raffinate contains a maximum of 1 g/l of lactic acid and the ammonium sulfate, and accompanying salts from the fermentation such as phosphates, nitrates and chlorides.

In order to accomplish the production of lactic acid in highly pure and polymerizable quality, because of residues of colored substances and accompanying substances still present, a two-stage purification by ion exchange and nanofiltration is added downstream of the SMB in process step c). These two stages can be arranged in any order. As ion exchange resins, depending on the chemical analysis of the impurities, cation and/or anion exchangers are possible. Here the same anion or cation exchange resins are used as in the SMB, or alternatively different ion exchange resins are used for the SMB. The nanofiltration serves mainly for the fine purification of the extract from the previous process steps, wherein the membranes have a separation size of 100 to 400 Da. It could be shown that a nanofiltration with a separation limit about 200 Da yields good quality results. During this, the process is operated such that the retentate from the nanofiltration is not more than 10% of the total throughput. The permeate is passed to the further process steps.

In further configuration of the purification process, the permeate from process step c) is passed to a first single or multistage evaporation. In this, evaporation to a concentration of 45 to 55 wt. % lactic acid takes place.

The preconcentrated and prepurified lactic acid solution resulting therefrom is then in process step d) once again subjected to ion exchange. Here also, in comparison to the previous ion exchange steps, the same chromatography resins or ones differing therefrom are used.

In process step f) of the process according to the invention, the purified lactic acid solution from process step e) is taken through to a lactic acid concentration of 80 wt. %, preferably of 88 to 92 wt. %.

Also a subject of the present invention is the use of the processed lactic acid according to the processes of claims 5 to 16 in the test for quality determination as claimed in claims 1 to 3. In this, on the basis of the quality criteria according to the invention, it can be assessed whether the lactic acid is suitable for polymerization.

Furthermore, the lactic aid produced according to the process as claimed in claims 5 to 16 can be used for the production of polylactides. Here the process for the production of polylactides preferably comprises the following process steps:
- Concentration of the lactic acid to 98 wt. %
- Precondensation of the concentrated lactic acid to an average molecular weight of 500 to 2000 g/mol
- Cyclizing depolymerization, wherein the lactide is generated,
- Purification of the lactide
- Ring opening polymerization
- Demonomerization
- Granulation and crystallization.

Below, the present invention will be illustrated in more detail on the basis of examples and figures.

DETAILED DESCRIPTION

Example 1

Polycondensation

Figure 1:
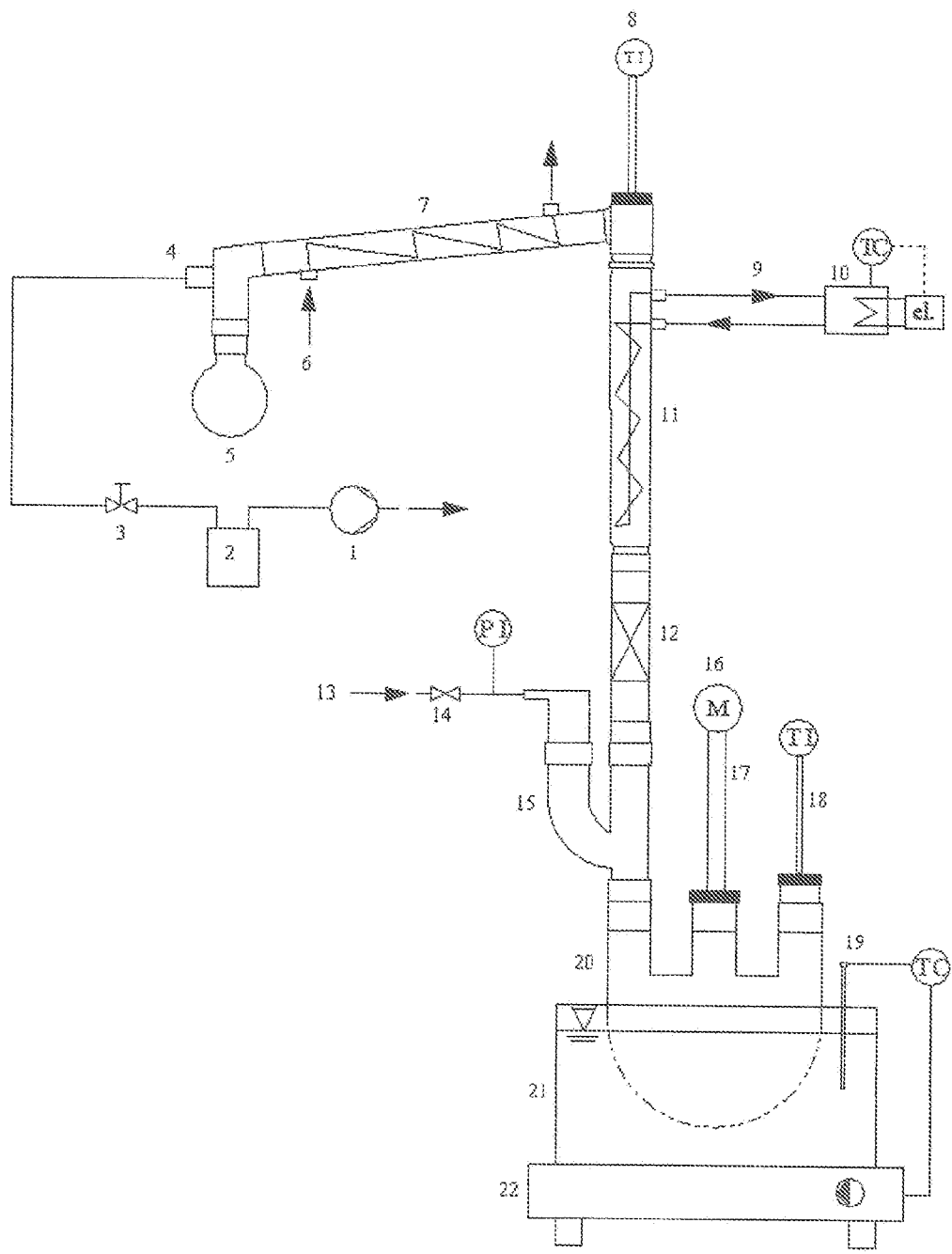
FIG. 1.: Schematic layout of a device for polycondensation of lactic acid, which is suitable for performing the test for quality determination of the lactic acid.

The polycondensation is performed on the basis of the device shown by way of example in FIG. 1. A three-necked round-bottomed flask 20 dips into a salt bath 21 which is heated with a hotplate 22. The three-necked round-bottomed flask 20 is weighed before dipping into the salt bath 21 and filled with a weighed out quantity of lactic acid. A two-necked flask 15 fitted onto on the three-necked round-bottomed flask serves for the introduction of nitrogen 13 via the valve 14. A reflux condenser 11 fitted onto the head of the two-necked flask 15 is kept at 50° C. to 70° C. by means of a heat transfer agent outlet 9 and a thermostat 10 with temperature-controlled water. Above the reflux condenser 11, there is placed a Liebig condenser 7 cooled with cold water 6, which discharges into a vessel. Side products of the polycondensation such as water collect there. Accompanying lactic acid is separated from water in the fractionating column 12 and flows back into the polycondensate. A vacuum pump 1 is connected to the apparatus via a side connector 4 at the outlet of the Liebig condenser 7. The vacuum is adjusted by means of a needle valve. Components not condensable at the condenser temperature are for example removed before the vacuum pump by means of a cold trap 2, which is connected to a valve 3, cooled for example with dry ice. To monitor the temperature of the process, various thermometers 8, 18 and 19 are provided. After the immersion of the three-necked round-bottomed flask 20 into the oil-bath, its temperature is increased stepwise from 120° C. to 180° C. over a time-span of 6 hours and the pressure lowered from 400 to 50 mbar. During this, the contents are stirred by means of the stirring device 16 and the stirrer shaft 17. After two hours, at a bath temperature of 150° C. and a pressure of 200 mbar, the first sample is taken and the catalyst metered in. As the catalyst, butyltin oxide (TW30 from the firm Acima, dissolved in a mixture of butanediol and methyl isobutyl ketone) is used, the concentration being 500 ppm of elemental tin based on the mass of the prepolymer. Further samples of the prepolymer are taken after 4 hrs (180° C., 200 mbar) and after 6 hrs (end of experiment, 180° C., 50 mbar).

Example 2

Depolymerization

Figure 2:
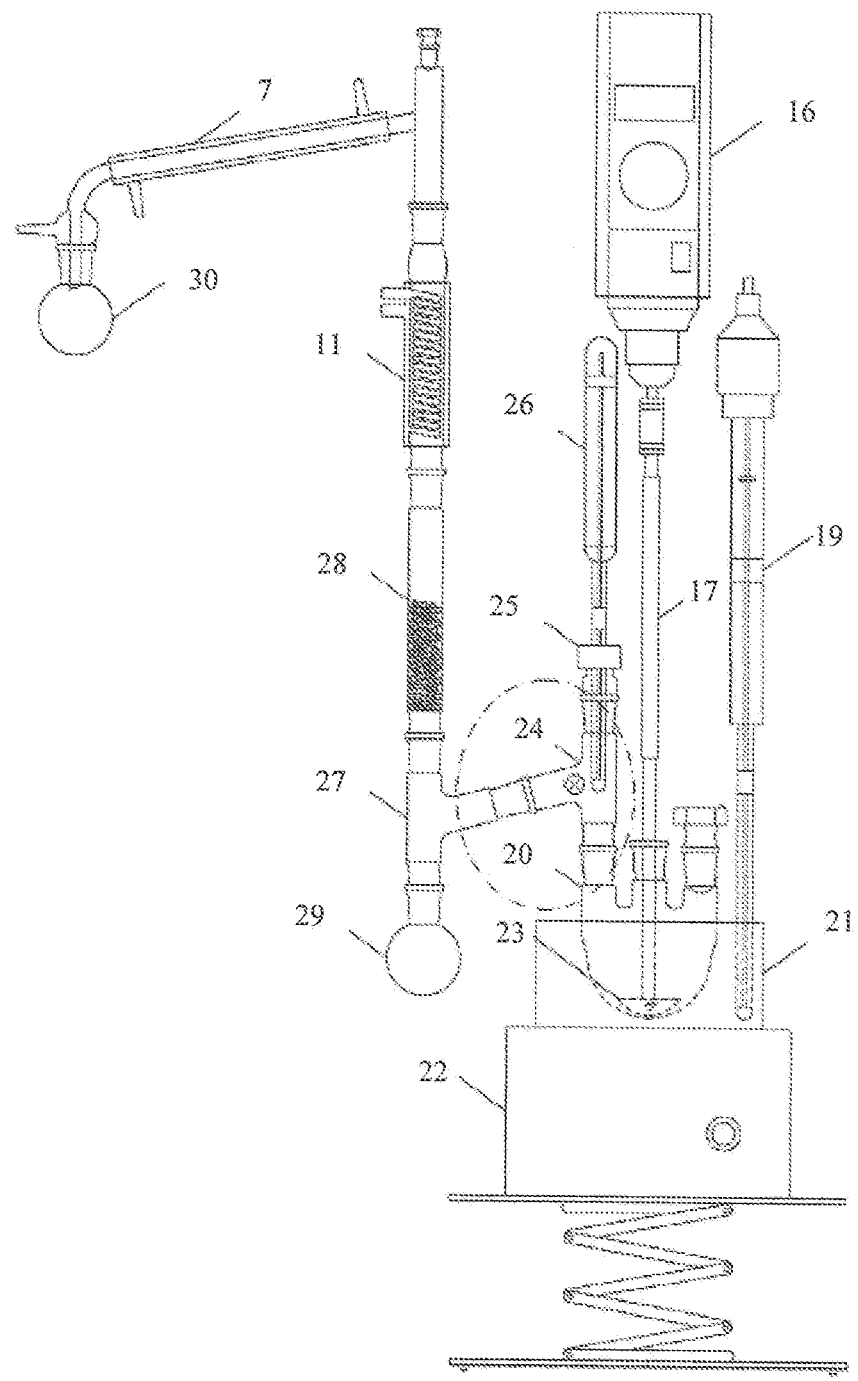
FIG. 2.: Schematic layout of a device for depolymerization of the polycondensate from the condensation, which is suitable for performing the test for quality determination of the lactic acid.

For the depolymerization, the prepolymer remains in the glass flask and the design is modified such that the fractionating column is arranged next to the three-necked round-bottomed flask 20 and connected with this via a bridging tube so that the vapor from the round-bottomed flask can flow from bottom to top through the fractionating column and no reflux from the fractionating column into the three-necked flask is possible. This is shown in FIG. 2. For this, the structure on the three-necked round-bottomed flask is as follows. The three-necked round-bottomed flask 20 is connected with a thermometer 26 via a first distillation head 24 and a threaded tube with screw closure 25. The first distillation head 24 is connected to a second distillation head 27, at the lower end whereof a hollow glass connector 29 is attached. Above the second distillation head 27, there is a packed column 28 and a reflux condenser 11. Above the reflux condenser 11 there is arranged a Liebig condenser 7 which discharges into a further hollow glass connector 30. During the reaction in the three-necked round-bottomed flask 20, the mixture is continuously stirred. This is effected via the stirring device 16 which is connected to the stirrer 23 via the stirrer shaft 17. The dilactide formed escapes in vapor form from the three-necked flask 20, condenses in the Liebig condenser 11 of the column and collects in the separate hollow glass connector 29 which closes the column at the bottom. Side products such as water and lactic acid condense in the Liebig condenser 7 at the head of the fractionating column and collect in the hollow glass connector 30. For this, the three-necked round-bottomed flask 20 is immersed in a salt bath 1 heated to 210° C., the pressure is adjusted to 200 mbar and the stirrer 4 started. The bath temperature is increased to 220° C. after 115 mins and maintained there. The pressure is reduced to 50 mbar after 30 mins, to 10 mbar after 45 mins and to 5 mbar after 165 mins. After 75 mins, the apparatus is vented and the hollow glass connector 29, in which the lactide formed collects, is changed. A further change is effected after 135 mins, so that a total of 3 lactide samples are produced. The temperatures in the apparatus are monitored via different thermometers 3 and 26.

Example 3

Separation of biomass and solids in the process according to the invention for the production of polymerizable lactic acid A fermenter liquor with a pH of 6.8 and a content of ammonium lactate of 12.2 wt. % calculated as lactic acid is passed for separation of the biomass via a separator.

The content of dry substance (DS) in the untreated liquor was about 6.9 g/l. After the separator, a content of DS of <0.03 g/l was measured in the clarified liquor. The solids content in the separated biomass was about 34.7 wt. %. The separator was run at ca. 360 l/hr.

According to the invention, the acidification of the fermenter liquor was effected with sulfuric acid in two stages, to pH 4.5 before and to pH 2.2 after the ultrafiltration.

The ultrafiltration was performed via a spiral-wound module. The membrane consisted of polyether sulfonate (PES) with an area of 7 $m^2$.

Owing to the good preclarification in the separator, very high flow values were achieved, which remained practically constant in the experimental period. The retentate had a very dark color and was subjected to diafiltration to avoid lactic acid losses.

The permeate was fed into the SMB after acidification to pH 2.2.

Example 4

SMB with anion exchange resin in the process according to the invention for the production of polymerizable lactic acid The fermenter liquor purified and acidified according to the process according to the invention as in Example 1 was passed through a SMB for the separation of lactic acid and ammonium sulfate. Deionized water was used as the eluent.

The columns of the SMB unit were filled with an anion exchange resin filled with lactate. Table 1 shows the results of the SMB:

TABLE 1

| Ion | Initial value | Extract | Raffinate | Efficacy |
|---|---|---|---|---|
| Sulfate | 75.084 mg/l | 650.3 mg/l | 34.697 mg/l | 98.34% |
| Lactate | 117.4 g/l | 70.2 g/l | 1.44 g/l | 97.77% |
| Volume | — | 1.8 l | 2.0 l | — |

Example 5

SMB with cation exchange resin in the process according to the invention for the production of polymerizable lactic acid In the same SMB unit, but with a fill of cationic exchange resin which was laden with ammonium ions, the following values were measured

TABLE 2

| Ion | Initial value | Extract | Raffinate | Efficacy |
|---|---|---|---|---|
| Sulfate | 71.580 mg/l | 190 mg/l | 46.920 mg/l | 99.54% |
| Lactate | 113.02 g/l | 74.26 g/l | 0.55 g/l | 99.34% |

The values show that the separative effect on the cation exchange resin is still better than in Example 2.

The sulfate is 99.54% eliminated and 99.34% of the lactic acid reach the extract.

Example 6

Nanofiltration and Ion Exchange in the Process According to the Invention for the Production of Polymerizable Lactic Acid In a laboratory apparatus fitted with a 0.07 m² flat membrane 250 Dalton, the effect of nanofiltration on the lactic acid solution produced according to the invention, which came from the SMB as an extract, was tested. The solution was at about 50° C. The pressure before the membrane was adjusted to 30 bar.

The permeate exhibits a markedly lighter color, the content of sugar, maltose was measured, greatly decreases and the sulfate content is also reduced. The reduction in the amino acids is also considerable.

Table 3 shows measured values regarding said effects:

TABLE 3

| Parameter | Initial value | Permeate |
|---|---|---|
| Yellowness Index (YI) | 28.55 | 2.4 |
| Maltose g/l | 1.1 | 0.05 |
| Sulfate g/l | 0.26 | 0.05 |
| Alanine | 0.22 | 0.10 |
| Aspartic acid | 1.23 | 0.35 |

In this example, after the nanofiltration the lactic acid solution had a concentration of 6 wt. %, a sulfate content of 18.2 mg/l, a phosphate content of 7.7 mg/l, a content of maltose of <0.01 g/l and a YI of 2.09.

For further removal of impurities, the lactic acid solution was passed through a combination of decolorant column, and cation and anion exchanger column.

Example 7

Evaporation, followed by ion exchange and further evaporation in the process according to the invention for the production of polymerizable lactic acid The lactic acid solution produced according to the invention, after the two-stage purification by nanofiltration and ion exchange, still contains a number of ions, small quantities of residual sugars and colorant substances.

For as complete as possible removal of all impurities, the lactic acid solution is now passed through a combination of decolorant column, and cation and anion exchanger column, evaporated to ca. 50 wt. % lactic acid and again passed through said combination of decolorant and ion exchanger columns.

After passage through the arrangement described above a 61 wt. % lactic acid with the following parameters was obtained:
Sulfate: 2.6 mg/l
Phosphate: 0.23 mg/l
Maltose: 0.04 g/l
YI: 0.72

The lactic acid solution was water clear even after passage through the second evaporation stage wherein a lactic acid concentration of 90 wt. % lactic acid was attained. The lactic acid thus purified fulfils the quality test according to the invention and exhibits a lactide yield of 91.7% and a racemization of 3.3% and is thus suitable as a starting product for PLA production.

Example 8

Description of a process for the production of polylactides, which uses the lactic acid which was generated by the process according to the invention for lactic acid production In this, reference is preferably made to a process which is disclosed in detail in WO2009/030397 A1.
a) Concentration of Lactic Acid As the starting material, lactic acid as yielded by the process according to the invention as claimed in one of claims 5 to 16 is used. In this, the separation of water and lactic acid is effected in a fractionating column. Also, vacuum is applied via a suction connector and the water arising in vapor form is condensed and removed at the top via a further connector. The introduction of the lactic acid is effected continuously in the process. The distillate is pure water, and the product arising in the bottoms is lactic acid with a concentration of more than 99 wt. %.

b) Precondensation

The concentrated lactic acid is converted into a prepolymer by polycondensation in a series of two reactors. The polycondensation proceeds under two different pressures and temperatures in order to optimize the reaction conversion. In the first reactor, the conditions are selected such that the evaporation of lactic acid is minimized at the same time the removal of water is facilitated. In the second step of the polycondensation, the reaction rate is increased by a higher temperature and at the same time the pressure is decreased in order further to reduce the water concentration in the melt. The average molecular weight (number average) of the prepolymer here lies between 500 and 2,000 g/mol.

3c) Cyclizing Depolymerization The prepolymer is in chemical equilibrium with the cyclic dimer of lactic acid, dilactide.

By adjustment of pressure and temperature in the depolymerization reactor it is ensured that the lactide is continuously formed from the prepolymer and evaporates. The depolymerization reactor has a condenser which partially condenses the reaction vapors: here, water and the major part of the lactic acid remain in vapor form and are in turn partly condensed in a condensation device. The condensate from the depolymerization reactor first and foremost contains lactide, lactoyllactic acid (the linear dimer of lactic acid) and higher linear oligomers.

d) Lactide Purification

During the ring opening polymerization, the attainable molecular weight and thus important mechanical properties of the polylactide depends on the degree of purity of the lactide. The hydroxyl groups of the lactic acid and lactoyllactic acid contained as impurities here serve as the starting point of the polymerization. The higher the concentration of the hydroxyl groups is in the lactide, the lower the attainable molecular weight of the polymer becomes. The concentration of the hydroxyl groups in the crude lactide after the cyclizing depolymerization is too high. The condensed lactide is purified to the required hydroxyl group concentration in a fractionating column. The purified lactide is taken off from the column as a side-stream. The distillate and the bottom product can be introduced into the process again at different locations.

e) Ring Opening Polymerization

The ring opening polymerization is performed in a reactor which is formed of a combination of a stirred vessel and a tubular reactor. In the first reactor, the low viscosity lactide is polymerized to PLA with a conversion rate of ca. 50-70%. Catalyst and additives are mixed homogeneously into the melt. In the tubular reactor, the polymerization reaction is continued until a chemical equilibrium between polymer and monomer is reached. The maximal conversion of the monomer is ca. 95%. During the polymerization, the viscosity increases to ca. 10,000 Pa sec.

e) Demonomerization

In order to obtain a stable polylactide, the monomer concentration of about 5 wt. % in the melt is too high. Consequently, a demonomerization must be performed. This is achieved by degassing of the melt, e.g. in a twin screw extruder. Owing to the fact that the ring opening polymerization is an equilibrium reaction, a stabilizer is added before the demonomerization in order to prevent renewed formation of the monomer during and after the degassing.

f) Granulation and Crystallization

Following the demonomerization, the melt is removed from the demonomerization apparatus and converted into granules. Here both strand granulation and also submerged hot-cut granulation can be performed. In both cases, the PLA granules must be crystallized before drying and packing. The crystallization is performed at elevated temperatures and with stirring.

The invention claimed is:

1. A process for separation and purification of polymerizable lactic acid from fermentation liquors, comprising:
    a) separating biomass and any solids from the fermentation liquor, in at least two successive stages;
    b) separating lactic acid solution from the biomass-free fermentation liquor by use of simulated moving bed chromatography (SMB);
    c) purifying the separated lactic acid solution by a first ion exchange step;
    d) subjecting the first-ion-exchange purified lactic acid solution to at least one of a first single or multistage partial evaporation step to obtain a lactic acid solution having less than a 100% concentration by weight of lactic acid;
    e) purifying the lactic acid solution further by a second ion exchange step;
    f) subjecting the second-ion-exchange purified lactic acid solution to at least one of a second single or multistage evaporation step.

2. The process of claim 1, wherein the process exhibits a dilactide yield of >90% and a racemization of <5%.

3. The process of claim 2, wherein the step of purifying the separated lactic acid solution by a first ion exchange step includes nanofiltering the lactic acid solution.

4. The process of claim 2, wherein the step of separating biomass and any solids from the fermentation liquor is effected in a first stage by at least one of a precoat, a microfiltration, and a centrifugation.

5. The process of claim 4, wherein the step of separating the biomass from the fermentation liquor is effected without decreasing the pH and without thermal inactivation.

6. The process of claim 4, wherein during the step of separating biomass and any solids from the fermentation liquor, the time between ending of the fermentation and the separation of the biomass is less than 2 hours.

7. The process of claim 4, wherein during the step of separating biomass and any solids from the fermentation liquor, the biomass concentration in the filtrate is not higher than 1 g/l.

8. The process of claim 2, wherein a second stage in the step of separating biomass and any solids from the fermentation liquor includes ultrafiltering the fermentation liquor by at least one of a single-stage or a two-stage ultrafiltration having filtration membranes with a separation limit of 10 kDa.

9. The process of claim 8, further comprising:
    recirculating a retentate from the second stage ultrafiltration back to the first stage in the step of separating biomass and any solids; and
    passing a permeate from the second stage ultrafiltration to subsequent process steps.

10. The process of claim 2, further comprising:
    adding concentrated sulfuric acid to the fermentation liquor from the first stage in the step of separating biomass and any solids, to create an acidified fermentation liquor having a pH of 4.4 to 4.6; and
    adding concentrated sulfuric acid to an ultrafiltration permeate from the second stage in the step of separating biomass and any solids, to create an acidified ultra permeate having a pH of 2.0 to 2.4, so that a salt of lactic acid contained in the purified fermentation solution is converted to lactic acid and salt is formed in the stoichiometric proportion, wherein the temperature of the acidified ultrafiltration permeate is kept in a range between 30° C. to 60° C.

11. The process of claim 8, wherein the step of separating lactic acid solution from the biomass-free fermentation liquor includes separating the ultrafiltration permeate in a simulated moving bed chromatography (SMB) into (a) an extract containing the major part of the lactic acid and (b) a raffinate containing the major part of ammonium sulfate and small quantities of accompanying salts, such as phosphates, nitrates and chlorides, wherein
   (i) the addition of the ultrafiltration permeate and an eluent is effected continuously in a permeate:eluent ratio of 1:1.5 to 1:2.5,
   (ii) the extract containing the lactic acid, having a content of lactic acid >1 g/l, and the raffinate are collected separately from one another, and
   (iii) the efficacy of the recovery of lactic acid from the ultrafiltration permeate is >95%.

12. The process of claim 2, wherein in the two steps of purifying lactic acid solution by each of the first ion exchange step and the second ion exchange step, a purification from anionic and cationic impurities is produced by cation exchangers and/or anion exchangers.

13. The process of claim 2, wherein in the step of subjecting the first-ion-exchange purified lactic acid solution to the at least one of the first single or multistage partial evaporation step, a single or multistage partial evaporation to a lactic acid concentration of 45 to 55 wt. % is achieved.

14. The process of claim 2, wherein in the step of subjecting the second-ion-exchange purified lactic acid solution to at least one of a second single or multistage evaporation step a single or multistage evaporation to a lactic acid concentration of 80 wt. % is achieved.

15. The process of claim 2 further comprising producing polylactides based on the purified lactic acid solution after subjecting the second-ion-exchange purified lactic acid solution to the at least one of the second single or multistage evaporation step.

16. The use process of claim 15, wherein producing the polylactides comprises:
   concentrating the lactic acid to 98 wt. %;
   performing precondensation on the concentrated lactic acid to achieve an average molecular mass of 500 to 2000 g/mol;
   performing cyclizing depolymerization on the precondensated lactic acid, wherein lactide is generated;
   purifying the lactide;
   conducting ring opening polymerization on the lactide to create polylactide;
   performing demonomerization on the polylactide;
   converting the polylactide to polylactide granules; and
   crystalizing the polylactide granules.

* * * * *